US012636263B2

(12) United States Patent
Xu et al.

(10) Patent No.: US 12,636,263 B2
(45) Date of Patent: May 26, 2026

(54) CAROTENOID COMPOUND COMING FROM PLANT AND CONTAINING NATURAL ASTAXANTHIN, PREPARATION METHOD THEREFOR, AND COMPOSITION

(71) Applicant: Zhejiang Medicine Co., Ltd. Xinchang Pharmaceutical Factory, Xinchang County (CN)

(72) Inventors: Xinde Xu, Xinchang County (CN); Bin Shao, Xinchang County (CN); Yongjian Peng, Xinchang County (CN); Shengnan Wang, Xinchang County (CN)

(73) Assignee: Zhejiang Medicine Co., LTD Xinchang Pharmaceutical Factory, Xinchang (CN)

( * ) Notice: Subject to any disclaimer, the term of this patent is extended or adjusted under 35 U.S.C. 154(b) by 785 days.

(21) Appl. No.: 17/946,485

(22) Filed: Sep. 16, 2022

(65) Prior Publication Data

US 2023/0172876 A1 Jun. 8, 2023

Related U.S. Application Data

(62) Division of application No. 15/024,783, filed as application No. PCT/CN2014/000862 on Sep. 23, 2014, now abandoned.

(30) Foreign Application Priority Data

Sep. 24, 2013 (CN) ........................ 201310440119.6

(51) Int. Cl.

| | |
|---|---|
| ***A61K 31/122*** | (2006.01) |
| ***A23K 20/179*** | (2016.01) |
| ***A23L 33/105*** | (2016.01) |
| ***A61K 8/9789*** | (2017.01) |
| ***A61K 36/71*** | (2006.01) |
| ***A61Q 19/00*** | (2006.01) |
| ***C07C 403/24*** | (2006.01) |

(52) U.S. Cl.

CPC .......... *A61K 31/122* (2013.01); *A23K 20/179* (2016.05); *A23L 33/105* (2016.08); *A61K 8/9789* (2017.08); *A61K 36/71* (2013.01); *A61Q 19/00* (2013.01); *C07C 403/24* (2013.01); *A61K 2236/33* (2013.01); *A61K 2236/37* (2013.01); *A61K 2236/51* (2013.01); *A61K 2236/53* (2013.01); *A61K 2800/10* (2013.01); *A61K 2800/43* (2013.01); *C07C 2601/14* (2017.05); *C07C 2601/16* (2017.05)

(58) Field of Classification Search

CPC .................................................... A61K 31/122

See application file for complete search history.

(56) References Cited

FOREIGN PATENT DOCUMENTS

CN 1472201 * 2/2004 ........... A61K 31/122

* cited by examiner

*Primary Examiner* — Paul V Ward

(74) *Attorney, Agent, or Firm* — Christopher Casieri

(57) ABSTRACT

The present invention provides a high-content carotenoid compound from *Adonis amurensis*. The content of the total carotenoid of the carotenoid compound is higher than 95%. The content of all-trans (3S, 3'S)-carotenoid is higher than 80%. The carotenoid crystals have a high purity, and can be used in multiple forms in the fields of a dietary supplement of a human being, a food additive, a feed additive and a cosmetic product. In addition, the present invention also provides a method for manufacturing the compound.

4 Claims, No Drawings

CAROTENOID COMPOUND COMING FROM PLANT AND CONTAINING NATURAL ASTAXANTHIN, PREPARATION METHOD THEREFOR, AND COMPOSITION

CROSS-REFERENCE TO RELATED APPLICATIONS

This application is a divisional of application Ser. No. 15/024,783, filed on Jul. 11, 2016, which is a national phase application of PCT/CN2014/000862, filed on Sep. 23, 2014, which claims priority to Chinese Application No. 201310440119.6 filed on Sep. 24, 2013.

FIELD OF THE INVENTION

The present invention relates to a carotenoid compound coming from plant extract with less impurity containing natural astaxanthin with high biological activities, and its preparation method and composition, and relates to the field of biochemistry.

BACKGROUND OF THE INVENTION

Astaxanthin's formula is $C_{40}H_{52}O_4$ and is referred to as 3,3'-dihydroxy-4,4'-diketo-β,β'-carotene, widely exists in nature, is an important substance of carotenoid, and has a higher physiological activity than other carotenoids. The molecular formula is as follows:

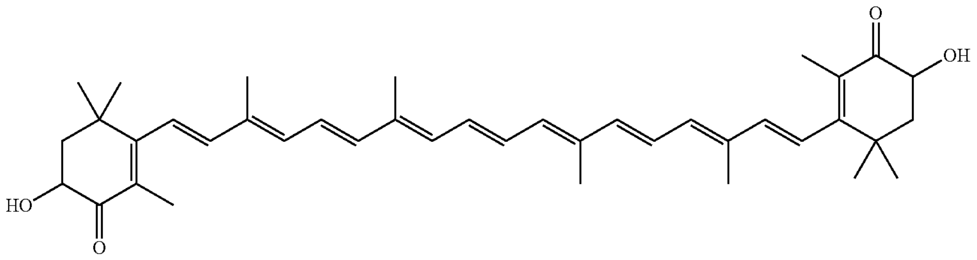

*trans*-astaxanthin

As for a kind of natural preparation, astaxanthin has broader uses and development prospects in various industries such as pharmaceuticals, aquacultures, foods, chemistries.

Astaxanthin plays a role in the body without being transformed into vitamin A, and has various excellent biological functions such as protecting retinas and central nervous systems, preventing UV radiation, preventing cardiovascular disease and enhancing immunity of organism etc. as for a kind of non-vitamin A source carotenoid.

First of all, astaxanthin is referred to as "super VE" and is substances with the most oxidizability so far, and is 1000 times as much as that of natural VE. Its molecular structure has long conjugated double bonds, and is coupled with a α-ketone hydroxyl composed of unsaturated keto group and hydroxyl at the end of carbon chain, and has lively electronic effects, to make astaxanthin easily react with radicals and clear them, and has strong antioxidant properties. Double blind human assays have proven that astaxanthin contributes to improve antioxygenic property of erythrocyte and reduce levels of phospholipid hydroperoxide.

At the same time, it is shown from immunological research that astaxanthin has a stronger ability of inhibiting cancer than that of β-carotene, can directly act on immune systems and induce tumor shrinkage. Astaxanthin has functions of improving anti-tumor immune response and reducing incidences of various cancers in mice such as gastric cancer, colon cancer, oral cancer and bladder cancer in a certain extent, reducing carcinogenicity of aflatoxin, and preventing from skin aging and skin cancer caused by light radiation as for a light protective agent.

Furthermore, astaxanthin has high immunomodulatory activities and promotes production of human immunoglobulins. Astaxanthin can effectively prevent from occurrence and spread of diseases after combining with its antioxidant function. Feeding astaxanthin can enhance antibody responses and humoral immunity, slow down reductions of immune ability, enhance functions of T cells in vivo, increase numbers of neutrophils, and participate in organism cellular immunity. Assays show that feeding astaxanthin can enhance antibody responses and humoral immunity, improve immunity of animals; enhance cellular immunity responses and humoral immune responses of dogs and reduce DNA damage and inflammation.

In addition, astaxanthin itself is bright red, and is the end of carotenoid synthesis in vivo, and has strong abilities of pigmentation. Astaxanthin can be directly stored and deposited in tissue without modification or biochemical conversion, and can be used as a functional pigment in various industrial fields after entering animal body. It is shown from a large number of animal assays that adding appropriate astaxanthin in baits can improve colors of skin and muscle, and enhance ornamental values and commodity values of aquatic animals. It may be found from feeding astaxanthin of *Euphausia superba* and opossum shrimp into the red carp that the pigmentation effect on fish skin is obvious and maintained.

Furthermore, astaxanthin also can enhance survival rates of fishes and shrimps, reduce infectious diseases, promote early embryonic developments; and have functions such as keeping fresh and preventing discoloration, off-flavor and metamorphism in food industry. It also can be applied in fields of cosmetics, because of its effects such as anti-oxidation, anti-wrinkle and anti-ultraviolet radiation. Astaxanthin is remarkably the only substance to effectively prevent from diabetic kidney damage. It has been found from several studies that astaxanthin also can prevent diseases such as arteriosclerosis, cataracts, cardiovascular disease, and used as nutritional supplements.

Astaxanthin has multiple double bonds in its molecular structural formula, correspondingly has cis- and trans-isomers. Generally speaking, all trans-isomers astaxanthin has the highest activity relative to cis-isomers, astaxanthin has two isomers as 9-cis and 13-cis, because of influences of spatial structure.

In addition, due to four chiral centers existing in its molecular structural formula, astaxanthin also has optical isomers. The main optical isomer includes three forms such as (3 R, 3 R)'-, (3 R, 3 S,' meso)- and (3 S, 3'S)-, and the molecular structure of the three isomers are shown below. Different sources of astaxanthin give different optical isomers. Different optical isomers have different physiological activities. Generally speaking, the bioavailability of (3 S, 3'S)-configuration in animal body is relatively high and is 15 wt % higher than the bioavailability of (3 R, 3 R)'-configuration. The molecular structural formula of astaxanthin of salmon is (3 S, 3'S)-configuration.

synthesis, which can lead to generation of some potential safety hazard and reduction of safety performance.

Natural astaxanthin often combines with protein in vivo to show different colors such as green, brown. Astaxanthin released is bright red after protein denaturation by heating. Its molecular formula has a hydroxyl group which easily combines with carboxyl to generate stable astaxanthin esters. Therefore most of natural astaxanthin exists in the states of astaxanthin esters, such as monadic ester, dibasic ester.

There are six sources from extraction of crustaceans animals and plants such as bacteria, protozoa, fungi,

1

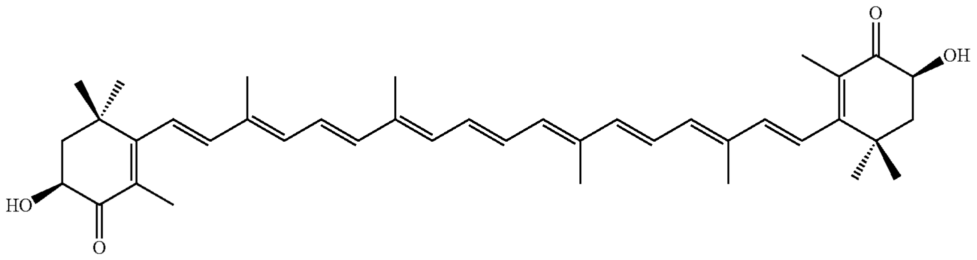

(3,S,3′S)

2

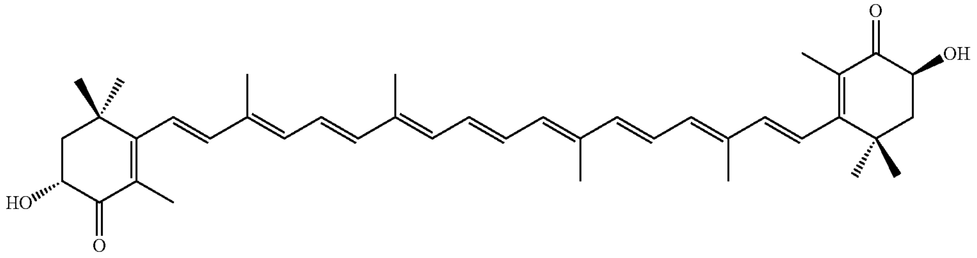

(3R,3′S; meso)

3

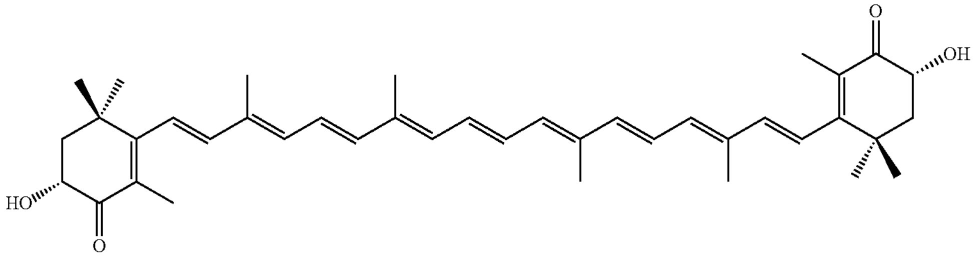

(3R,3′R)

At present, astaxanthin is mainly produced in two ways such as chemical synthesis and natural extraction. Astaxanthin prepared by chemical synthesis is expensive and has significant differences in molecular structures, biological functions, application effects and biological safeties. Synthetic astaxanthin is a mixture of three different configurations wherein most of them are (3R and 3'S). Synthetic astaxanthin obviously has stabilities and antioxidant activities lower than that of natural astaxanthin, and the effects of biological absorption and pigmentation of synthetic astaxanthin are also worse than that of natural astaxanthin. And synthetic astaxanthin can not be converted into natural astaxanthin in animal bodies. On the other hand, pollutions and impurities are inevitably produced in the process of microalgae in natural astaxanthin. Wherein the bacteria thalli has basically no use value because of its slow growth and low synthesis. And astaxanthin of protozoa is not synthesized by itself, and consequently is not considered.

It have been reported from domestic and international literatures that producing astaxanthin from microalgae is to culture product of *Haematococcus pluvialis*. Natural astaxanthin obtained by the method has with predominance of (3S, 3'S)-configuration, has basically the same molecular structure of astaxanthin as that of salmon organisms, and has higher activity. However, it is difficult to establish a stable and efficient production technology system, because the *Haematococcus pluvialis* is sensitive to environment, and susceptible to protozoa and bacterial contamination.

Astaxanthin can be accumulated and cultured from products of some fungi such as *Phaffia rhodozyma*. It would be required to add a lot of carbon source and nitrogen source, especially has high price organic nitrogen source (yeast extract and peptone, etc.) so as to improve astaxanthin yields of *Phaffia rhodozyma* and overcome disadvantages of low content. Consequently it increases production costs and is adverse to commercial production. At present, studies on industrial production of astaxanthin by uses of fungi focus on breeding of high-yield strain, exploration on fermentation process and regularity, studies on cheap fermentation substrates and its physiological function, etc.

Many factors restrict astaxanthin extraction including shellfish waste such as shrimp shell being perishable, big volume, relatively high transportation cost, low content levels of astaxanthin with large changes, binding state of astaxanthin, particle size shell etc. No better method with industrial scales of producing astaxanthin from these waste has been found at present.

Nowadays, natural astaxanthin is mainly obtained by culture of *Haematococcus pluvialis*, fermentation of *Phaffia rhodozyma*, and extraction of aquatic products such as shrimp and crab. However, it would be difficult to realize large-scale production because of some deficiencies such as culture conditions, high costs, hard extraction conditions. It should be noted that some plants also contain astaxanthin and carotene ketone, in particular, for the genus *Ranunculaceae* plants such as *Adonis amurensis, Adonis vernalis, Adonis aestivalis, Adonis palaestinia*, besides animals and microorganisms. Petals of *Ranunculaceae Adonis* genus also contain a large amount of astaxanthin. To extract natural astaxanthin by planting a large amount of *Adonis amurensis* with high-content of natural astaxanthin is a up-and-coming method.

Production of natural astaxanthin by extracting from plant tissue such as *Adonis amurensis* (also called "*Adonis*") is a up-and-coming method and is different from production method by culture of algae, fermentation of fungus, and extraction of shellfish. On the one hand, natural astaxanthin obtained by this method has high activities, and its molecular structure of astaxanthin is basically consistent with that of astaxanthin in organisms of salmon. On the other hand, cultivation condition of *Adonis amurensis* is simple, to be easy to realize large-scale cultivation and realize industrial production.

*Adonis amurensis* (scientific name: *Adonis amurensis*), another name false hellebore or *Adonis aestivalis*, is a perennial herbaceous plant of *Adonis* genus, and mainly distributes in northeast China, South Korea, Japan, Siberia. Flowering phase is a cold period of early spring from February to April. Most of *Adonis amurensis* are basically yellow flowers with 3 cm to 4 cm, flower diameter modified by gene may have an increased diameter. Most of *Adonis amurensis* of European varieties are red flowers, other varieties are green, white, orange and double flowers. *Adonis amurensis* contains natural astaxanthin, wherein the content of astaxanthin in the dried flower is about 2 wt %.

Carotenoid of *Adonis amurensis* contains 75-90 wt % of monoester, diester or free astaxanthin, 5~10 wt % of lutein and adonirubin, and less than 1 wt % of 3-hydroxyechinenone, 4-hydroxyechinenone and β-carotene, etc.

Generally carotenoid is extracted from *Adonis amurensis* by organic solvents or super critical method to obtain *Adonis* oleoresin (also called a "*Adonis extractum*") containing less than 10 wt % of astaxanthin, and astaxanthin in oleoresin also exists in the form of diester or monoester. As mentioned above, the bioavailability of astaxanthin in esterified state can be affected in animal body. It is necessary to obtain free natural astaxanthin by saponifying astaxanthin. Astaxanthin is a very unstable substance, with high antioxidant activity, and very easily oxidized to semi-astacene under the conditions of alkaline environment or oxygen or heating, thereby affect its bioactivity. The molecular structural formula of semi-astacene and astacene are shown in the figures below:

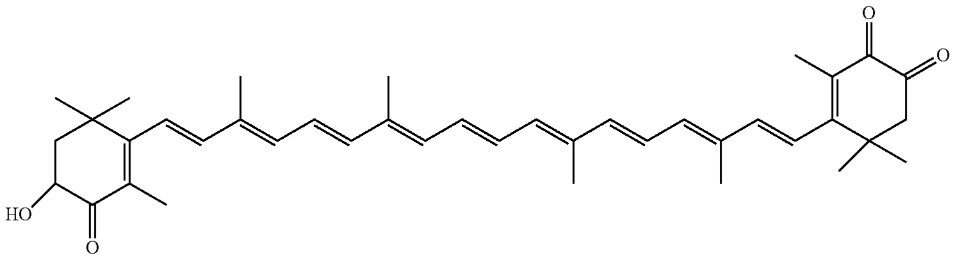

Semi-astacene ($C_{40}H_{50}O_4$)

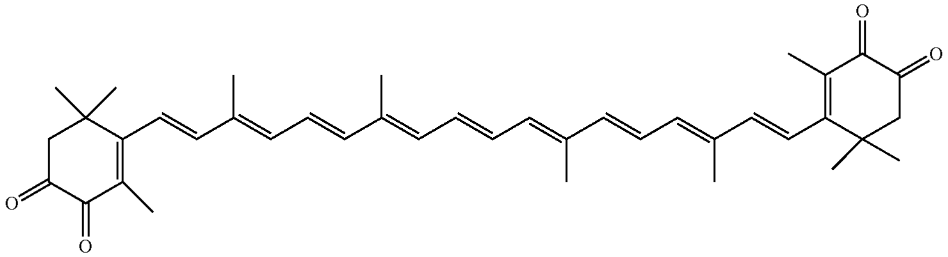

Astacene ($C_{40}H_{48}O_4$)

Semi-astacene and astacene also belong to carotenoid, some aquatic animals such as shrimp and crab show cyan when alive and show red after cooking. It is because astaxanthin of shrimp and crab is changed to semi-astacene and astacene after heating. There are a large number of semi-astacene and astacene in human diet, and a relatively large number of semi-astacene and astacene exists in human blood without security problem. Its antioxidant activity is reduced when astaxanthin is oxidized to semi-astacene and atacene. It should try to prevent from astaxanthin to semiastacene or atacene during processing if astaxanthin is used as a dietary supplement or a coloring agent.

So some conditions such as appropriate solvent, alkali concentration, saponification time, reaction temperature and substrate concentration must be controlled in the process of hydrolyzing astaxanthin diester into free astaxanthin, to maintain a balance of, reaction, and reduce generation of semiastacene and atacene in the reaction process, to keep strong antioxidant activity of astaxanthin products.

Alternately, there is other carotenoid such as adonirubin, lutein, echinenone besides astaxanthin in carotenoid of *Adonis amurensis*. These carotenoids are found in daily dietary composition and in human blood. But these carotenoids should be removed in the process of extraction and purification of astaxanthin, in order to improve proportion of astaxanthin in the total carotenoid.

carotenoid containing 80 wt % astaxanthin in the form of fatty acid ester in the product.

The Chinese patent CN101863812A also disclosed a method of preparing ointments containing astaxanthin by extracting *Adonis* dried flower with a mixture solvent of propane and butane and purifying the ointments by silica gel column to obtain a product with high purity. The astaxanthin of the product is also in the form of fatty acid ester.

The Chinese patent CN 1234687C described a method of extracting astaxanthin from *Adonis amurensis* to obtain 5 wt % of the total carotenoid in the final dried product, and 80 wt % of astaxanthin fatty acid ester in the total carotenoid.

The above-mentioned published applications or patents mainly relate to improvement of plant species to improve astaxanthin contents in the flowers, or processes of extracting *Adonis amurensis* oleoresin with lower levels of astaxanthin from *Adonis amurensis*, purifying *Adonis amurensis* oleoresin by silica gel column chromatography to finally obtain low levels of the total carotenoid with content of 5~10 wt %, without research or definition for carotenoid with lower activity.

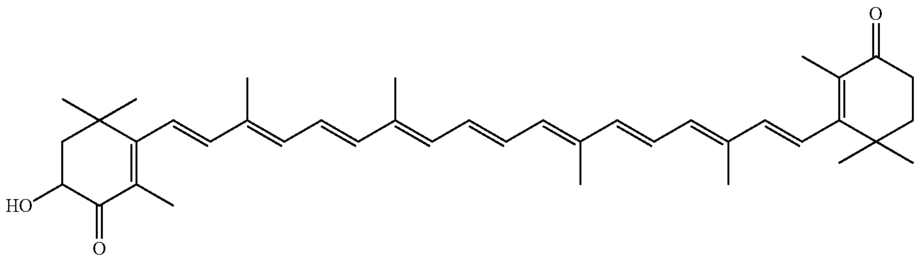

Adonirubin (Adonirubin, 3-hydroxy-β,β′-carotene-4,4′-dione, $C_{40}H_{52}O_3$)

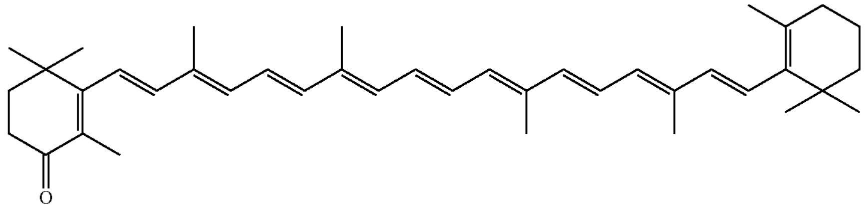

Echinenone (Echinenone, β,β-Carotene-1-one, $C_{40}H_{54}O$)

In previous literature, it was reported that natural astaxanthin was extracted from *Adonis amurensis*. US2006/0260010A1 discloses plantation of new modified plant of *Adonis palaestina* to increase astaxanthin content of flowers, and methods of extracting astaxanthin from flowers.

The application more detailedly describes variety improvement of *Adonis amurensis*, flower characteristics, contents of harmful material composition of cardenolide, forms of astaxanthin in flowers and compositions of other carotenoid, and wherein describes that contents of *Adonis* oleoresin containing astaxanthin obtained by supercritical CO2 extraction is 5 wt %~10 wt % and the purity of product is not high. However it was not mentioned how to remove impurities in *Adonis* oleoresin or Astaxanthin crystal containing Astaxanthin.

U.S. Pat. No. 5,453,565 revealed a method of extracting astaxanthin from *Adonis amurensis* by cultivating *Adonis amurensis* genus having at least 16 petals per flower head. The product obtained by the method is in *Adonis amurensis* oleoresin form, and the *Adonis amurensis* oleoresin containing low levels of astaxanthin are purified by silica gel column chromatography to obtain 20 wt % of the total On the other hand, the bioavailability of free astaxanthin is higher than that of astaxanthin in the form of fatty acid ester in vivo, is generally higher than 15% (Johnson and the an. Crit. Rev. Biotechnol, 1991). So it would improve the bioavailability of astaxanthin if the astaxanthin fatty acid ester is saponified to free astaxanthin. On the other hand, these impurities including other carotenoid should be removed in the process of saponification of astaxanthin fatty acid and subsequent purification. Especially the appropriate reaction conditions should be selected to reduce semi-astancene and Atacene, to maintain antioxidant activities of astaxanthin.

SUMMARY OF THE INVENTION

The present invention provides a carotenoid compound coming from plants containing natural astaxanthin and a preparation method thereof to overcome the deficiencies of the prior art.

According to one aspect of the present invention, the present invention provides a high-content carotenoid compound from flower, stem and fruit of *Adonis amurensis*, the content of the total carotenoid in the high-content carotenoid compound is higher than 95 wt %, wherein the proportion of all-trans (3S, 3'S)-astaxanthin in the total carotenoid is higher than 80 wt %, the all-trans (3S, 3'S)-astaxanthin has the molecular structure as shown in formula (I):

eficial to dissolution of astaxanthin fatty acid ester of the reaction substrates, the astaxanthin of the reaction product has low solubility in it, in order to facilitate the reaction and precipitate carotenoid crystals in the reaction process after completion of the reaction.

(I)

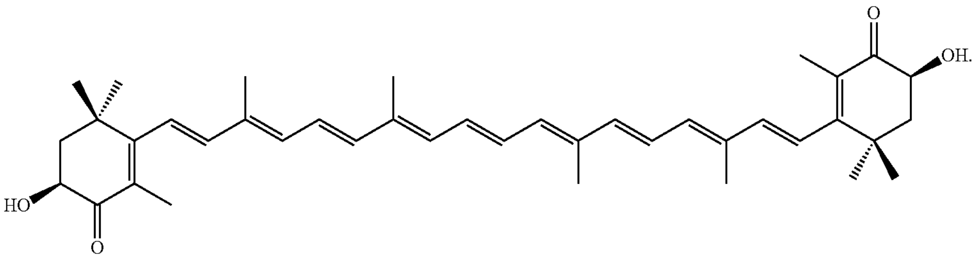

Preferably, the high-content carotenoid comprises semi-astacene, astacene and adonirubin.

Preferably, in the high-content carotenoid compound, the proportion of the total content of semi-astacene and astacene in the total carotenoid is less than 10 wt %, and the proportion of adonirubin in the total carotenoid is less than 10 wt %.

According to another aspect of the present invention, the present invention provides a method of preparing a high content carotenoid compound by using *Adonis amurensis* extract as raw materials, and the method comprises the following steps:

(a) mixing *Adonis amurensis* extract with alcohols solvent and fully dissolving, to obtain a mixed solution;

(b) heating the mixed solution of the step (a) to 25~75° C., and dropwise adding an alkali solution to the reaction, and the reaction time is 0.5~6.0 hr;

(c) adding a mixture of alcohols solvent and water to obtain a reaction solution, after completion of the step (b);

(d) filtering the reaction solution of the step (c) to obtain a filter cake, and then washing the filter cake with a mixture of alcohols solvent and water; and (e) drying the filter cake of the step (d) in vacuum to obtain a carotenoid compound;

wherein in the high-content carotenoid compound, the content of the total carotenoid is higher than 95 wt %, the proportion of the all-trans (3S, 3'S) astaxanthin in the carotenoid is higher than 80 wt %, the all-trans (3S, 3'S)-astaxanthin has the molecular structure as shown in formula (I):

Preferably, the ratio of volume of the alcohols solvent to the weight of *Adonis amurensis* extract in the step (a) is 5~50 times. More preferably, the ratio of volume of the alcohols solvent to the weight of *Adonis amurensis* extract in the step (a) is 25~40 times. If an amount of the solvent is too large, it is adverse to the reaction and prolong the reaction time and increase amounts of alkali. If an amount of the solvent is too small, a concentration of the reaction is too high. More importantly, increasing concentration of alkali in the reaction system makes more impurities generate, and then it is adverse to improve the purity of final products.

Preferably, the alkali solution in the step (b) is sodium hydroxide solution, potassium hydroxide solution or sodium methoxide solution.

Preferably, the concentration of the alkali solution of the reaction mixture in the step (b) is 0.01~2.50 mol/L after completion of adding dropwise the alkali solution. More preferably, the concentration of the alkali solution of the reaction mixture in the step (b) is 1.00~2.00 mol/L after completion of adding dropwise the alkali solution. The alkali concentration of the reaction system is critical, because firstly the saponification is not complete if alkali concentration is low, and it takes a long reaction time, secondly, it is easy to produce oxidation of astaxanthin to semi-astancene and atacene, to reduce purities of astaxanthin in final products if alkali concentration is too high. Consequently, the alkali concentration of the reaction system of the present invention is 0.01~2.50 mol/L, preferably, 1.00~2.00 mol/L. Some general separation measures such as using filter aids, changing the acidity-basicity and other measures in the process are used for increasing separation efficiency.

(I)

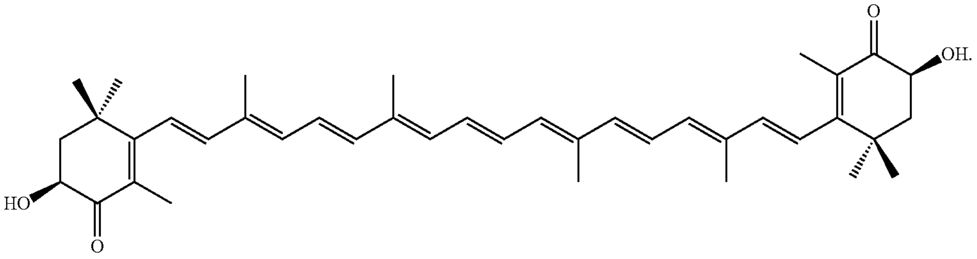

Preferably, the alcohols solvent of the step (a) is ethanol, propylene glycol or glycerol. The alcohols solvent is ben- Preferably, the volume ratio of alcohols solvent to water in the step (c) is 1:5~10. Preferably, the volume ratio of alcohols solvent to water in the step (d) is 2~3:1. The content of the total carotenoid and proportion of astaxanthin therein in the final product may be adjusted by adjusting the proportion of alcohols solvent to water and their total amount. The more the usage of the mixture solution is, the higher the percentage of alcohols solvent is, and then the higher the total carotenoid content is in the final product, and the higher the proportion of astaxanthin is. But it affects yields of final products.

According to another aspect of the present invention, the present invention provides a composition comprising the high content carotenoid compound for the preparation of foods, feed additives, dietary supplements, and cosmetics. Preferably, the composition further comprises of the group consist of vegetable oils, modified starch, sucrose, dextrin, and other food accessories.

Application form of astaxanthin may be in the form of oil, that is, the astaxanthin is dispersed in vegetable oil. And the application form of astaxanthin also may be in the form of powder, that is, after mixing with one or more selected from gelatin, modified starch, dextrin, sucrose and other auxiliary materials, the astaxanthin is embedded by a microcapsule emulsion technology in order to obtain astaxanthin in the form of microcapsule powder with good stability.

It may be seen from it that the preparation method of the high content carotenoid compound by using *Adonis amurensis* as raw material of the present invention only relates to a saponification, and then after the saponification, washing with a mixture of water and ethanol for several times to remove impurities in amorphous state to obtain a carotenoid compound containing astaxanthin, and further obtains a high content carotenoid compound by vacuum drying. No additional crystallization and purification steps is used in the whole process and no silica gel column chromatography process reported by the prior art is used. Most of another carotenoid impurities is removed, the content of semi-astacene and atacene is little and the final product maintains high biological activity. So the process is suitable for industrial production.

Thus the content determined by UV spectrophotometry is higher than 95 wt %, often higher than 97 wt %, and the content of all trans (3 S, 3 S)-astaxanthin analyzed by HPLC is higher than 80 wt %, and the remainders are calendulin, semi-astacene, astacene, echinenone or hydroxyechinenone, in the carotenoid compound obtained by the method of the present invention. These carotenoids are dietary sources and can be detected in human blood, and no security risk is present in the content. Also, no safety issues is present in the products, because ethanol is only used as solvents of the process, without uses of any other toxic and harmful organic solvent, and without other chemical impurities. Besides, the method is convenient to operate, and suitable for large-scale commercial production, because no additional purification steps such as column separation, multiple recrystallization are used in the process besides one step reaction.

DETAILED DESCRIPTION OF THE PRESENT INVENTION AND PREFERRED EMBODIMENTS THEREOF

Hereafter, the present invention will be described specifically with reference to examples. The examples are given only for illustration of the technical solution of the present invention and should not be construed to limit the present invention.

Firstly, the detection method of the total carotenoid content in crystals of the present invention is that determining the content of the total carotenoid by ultraviolet-visible spectrophotometry (UV). 20 mg of samples to be tested are weighed and added into a 100 ml brown volumetric flask, and 10 ml of chloroform are added to the brown volumetric flask to dissolve, and then n-hexane is added to constant volume, shaken well to obtain a mixture solution. 1 ml of the mixture solution is added to a 100 ml volumetric flask, and 4 ml of chloroform is added, then hexane is added to constant volume to a scale. The absorbance value of the solution is determined at 470 nm by ultraviolet-visible absorption photometer, and n-hexane is used as a blank.

The content C of the total carotenoid is C=A*10000/(2100*W), wherein A is an absorbance, W is sample weight.

In addition, the condition of detecting a proportion of astaxanthin in the total carotenoid of the present invention is as follows: HPLC chromatographic column: Eclipse XDB—C18, 5 μm, 4.6×150 mm; Mobile phase: methanol/water=95/5 (V/V); Flow rate: 1 ml/min; Column temperature: 25° C.; Detection wavelength: 478 nm.

The condition of determining chiral of astaxanthin of the present invention is as follows: chromatographic column: CHIRALPAK IC (0.46 cm×25 cm×5 μm); Mobile phase: ACN/MtBE=65/35 (v/v); Flow rate: 1 ml/min; Detection wavelength: 478 nm; Column temperature: 25° C.

Example 1

50 g (UV content is 10.5 wt %) of *Adonis amurensis* extract (*Adonis amurensis* extract is obtained by extracting *Adonis amurensis* dried granules with a mixture of propane and butane and then is volatilized) is added to 2500 ml of absolute ethanol, heated to 75° C. under stirring, kept for 1.0 hr to fully dissolve the *Adonis amurensis* extract. 432 ml of NaOH solution with 45% of the mass concentration (w/w) is added dropwise to form a reaction mixture solution, and the alkali concentration of the reaction mixture solution is 2.0 mol/L after completion of adding, and stirred at 75° C. for 4.0 hr. 5000 ml of deionized water and 1000 ml of ethanol are added to it, and then a dark red crystal is precipitated after slowly stirring for 1.0 hr. After filtration, a filter cake is washed with a mixture of ethanol and deionized water (the ratio of ethanol to deionized water is 2:1) for twice, 600 ml of the mixture of ethanol and deionized water per time, to obtain a crystal, the crystal is dried in vacuum, to eventually obtain 3.5 g of a dark purple carotenoid crystal.

Its maximum absorption wavelength of the carotenoid crystal by UV detection is at 470 nm, its content is 97.5 wt %, the ratio of astaxanthin analyzed by HPLC is 82.5 wt %, and, 98 wt % of the astaxanthin according to chiral HPLC analysis is (3 S, 3'S) configuration, 2 wt % of the astaxanthin is (3S, 3'R)' configuration.

At the same time, HPLC/MS analysis shows that there are all-trans atacene (6.81 wt %), and 9-cis semi-astacene and 13-cis semi-astacene (respectively 1.65 wt % and 1.65 wt %), as well as adonirubin (7.51 wt %), hydroxyechinenone (0.85 wt %) in the carotenoid crystal, besides all-trans astaxanthin. The total carotenoid composition in the crystal is shown in Table 1.

TABLE 1

| Various of carotenoid composition in the carotenoid crystal obtained from Example 1 Carotenoid composition (wt %) in carotenoid compound from adonis amurensis | |
|---|---|
| all-trans-(3S,3'S)-astaxanthin | 80.85 |
| all-trans-(3S,3'R)-astaxanthin | 1.65 |
| Total of all-trans-astaxanthin | 82.5 |
| all-trans-semiastacene | 6.81 |
| 9-cis-semiastacene | 1.65 |
| 13-cis-semiastacene | 0.46 |
| Adonirubin | 7.51 |
| Hydroxyechinenone | 0.85 |
| other carotenoid | 0.22 |

Also, as shown in Table 2, a relative content of each composition in carotenoid crystal of the final product is changed by changing a proportion of solvent to amount of adding alkali, without changes of other conditions.

TABLE 2

Influences of solvent ratio and alkali concentration on various of carotenoid

| Comparative examples | Alkali concentration of the final reaction solution (mol/L) | Proportion of alcohols solvent to raw materials | Proportion of various carotenoid composition of Crystals (wt %) all-trans-astaxanthin | Semi-astacene | astacene | adonirubin |
|---|---|---|---|---|---|---|
| 1 | 2.5 | 25 | 78.8 | 5.3 | 3.4 | 8.5 |
| 2 | 1.0 | 40 | 83.2 | 4.7 | / | 5.2 |
| 3 | 0.01 | 5 | 86.3 | 2.5 | / | 4.8 |

In comparative example 1, due to high concentration of alkali, part of semi-astacene are oxided into astacene, and proportion of adonirubin is also increased at the same time. It would be a reason to result in increasing relative contents of other carotenoid after degradation of parts of astaxanthin. In comparative example 3, the proportion of impurities such as semi-astacene, adonirubin are lower, and the proportion of all-trans astaxanthin is higher, because the alkali concentration is too low, there are still a large part of raw material not to have reacted completely after 6 hr and the yield of the final product is low.

Example 2

100 g of *Adonis amurensis* extract (UV content is 10.5 wt %) is added to 3000 ml of glycerol, heated to 60° C. under stirring, and kept for 1.0 hr to fully dissolve the *Adonis amurensis* extract. 1000 ml of $CH_3ONa$ solution with the mass concentration of 25% (w/w) is added dropwise to form a reaction mixture solution, and the alkali concentration of the reaction mixture solution is 1.16 mol/L, and stirred at 60° C. for 0.5 hr. 6000 ml of deionized water and 1000 ml glycerol is added to it, and then a dark red crystal is precipitated after slowly stirring for 1.0 hr. After filtration, a filter cake is washed with a mixture of glycerol and deionized water (the ratio of glycerine and deionized water is 3:1) for twice, 500 ml of the mixture of glycerol and deionized water per time, to obtain a crystal, the crystal is dried in vacuum, to eventually obtain 4.8 g of a dark purple carotenoid crystal.

Its maximum absorption wavelength of the carotenoid crystal by UV detection is at 470 nm, its content is 98.2 wt %, the ratio of astaxanthin analyzed by HPLC is 87.1 wt % and 97 wt % of the astaxanthin according to chiral HPLC analysis is (3 S, 3'S) configuration, 3 wt % of the astaxanthin is (3S, 3'R)' configuration.

At the same time, HPLC/MS analysis shows that there are all-trans atacene (3.81 wt %), and 9-cis semiastacene and 13-cis semiastacene (respectively 1.01 wt % and 0.26 wt %), as well as adonirubin (5.81 wt %), hydroxy echinenone (0.75 wt %) in the carotenoid crystal, besides all-trans astaxanthin. The total carotenoid composition in the crystal is shown in Table 3.

TABLE 3

| Various of carotenoid composition in the carotenoid crystals obtained from Example 2 Carotenoid composition (wt %) in carotenoid compounds from adonis amurensis | |
|---|---|
| all-trans-(3S,3'S)-astaxanthin | 84.49 |
| all-trans-(3S,3'R)-astaxanthin | 2.61 |
| Total of all-trans-astaxanthin | 87.1 |
| all-trans-astacene | 3.81 |
| 9-cis-semiastacene | 1.01 |
| 13-cis-semiastacene | 0.26 |
| Adonirubin | 5.81 |
| Hydroxyechinenone | 0.75 |
| other carotenoid | 1.26 |

Example 3

100 kg *Adonis amurensis* extract (UV content is 10.5 wt %) is added to 5000 L of propylene glycol, and is fully dispersed under stirring at 25° C. 123 L of KOH solution with a mass concentration of 25% (w/w) is added dropwise, and is stirred at 25° C. for 2.5 hr. After sampling and analysis with HPLC, it is found that the reaction is not complete, and the reaction is continued for 3.5 hr. After completion of the reaction monitored by HPLC, 5000 L of deionized water and 500 L of propylene glycol are added to it to terminate the reaction. After stirring slowly for 1.0 hr, a dark red crystal is precipitated. After filtration by pressure, a filter cake is washed with a mixture of propylene alcohol and deionized water (the ratio of propylene alcohol to water is 2:1) for twice, 600 ml of the mixture of propylene alcohol and deionized water per time, to obtain a crystal, the crystal is dried in vacuum, to eventually obtain 6.8 Kg of a dark purple carotenoid crystal.

Its maximum absorption wavelength of the carotenoid crystal by UV detection is at 470 nm, its content is 94.9 wt %, the ratio of astaxanthin analyzed by HPLC is 87.4 wt %, and the 91 wt % of astaxanthin according to chiral HPLC analysis is (3 S, 3'S) configuration, the 9 wt % of astaxanthin is (3S, 3'R)' configuration.

At the same time, HPLC/MS analysis shows that there are all-trans atacene (5.23 wt %), and 9-cis semiastacene and 13-cis semiastacene (separately 0.85 wt % and 0.23 wt %), as well as adonirubin (4.32 wt %), hydroxy echinenone (0.68 wt %) in the carotenoid crystal, besides all-trans astaxanthin. The total carotenoid composition in the crystal is shown in Table 4.

TABLE 4

Various of carotenoid composition in the carotenoid crystals obtained from Example 3
Carotenoid composition (wt %) in carotenoid compounds from adonis amurensis

| | |
|---|---|
| all-trans-(3S,3'S)-astaxanthin | 79.53 |
| all-trans-(3S,3'R)-astaxanthin | 7.87 |
| Total of all-trans-astaxanthin | 87.4 |
| all-trans-astacene | 5.23 |
| 9-cis-semiastacene | 0.85 |
| 13-cis-semiastacene | 0.23 |
| Adonirubin | 4.32 |
| Hydroxyechinenone | 0.68 |
| other carotenoid | 1.29 |

It may be seen from it that a mixture solution of alcohols solvent and water is added to terminate the reaction after completion of the reaction of the present invention, and the content of the total carotenoid and the proportion of astaxanthin of the final products can be adjusted by adjusting the proportion and the total amount of alcohols solvent and water. The more the usage of the mixture solution is, the higher the percentage of the alcohols solvent is, and then the higher the total carotenoid content in the final product is, and the higher the proportion of astaxanthin is. But it affects the yield of final products.

Example 4

Preparation of Oral Preparation of Natural Astaxanthin

Carotenoid is a kind of liposoluble dietary component and is often combined with lipoproteins in human blood. So carotenoid is mixed with a small amount of vegetable fat when oral administration, or is used with food containing a certain amount of grease when oral administration. It will greatly enhance absorption and bioavailability of the carotenoid. Carotenoid is mixed with modified starch and grease, and then emulsified and dispersed to obtain nanoscale particles, and afterwards embedded by common microcapsule emulsion technology in order to obtain astaxanthin. It can not only improve the stability of carotenoid, but also improve the absorption and bioavailability in vivo.

We have developed the following two dosage forms as follows by using the carotenoid crystal containing natural astaxanthin obtained from Example 2.

(1) 55 g of the carotenoid compound crystal containing natural astaxanthin are adequately grinded to make particles with 3 μm of particle size, and then mixed with 200 g of olive oil under stirring to make particles uniformly disperse to obtain an oil suspension. The content of the total carotenoid of the oil suspension is 20 wt %, wherein natural astaxanthin is 175 mg/g. After filling with nitrogen and packaging closely, the change of the total carotenoid and astaxanthin in the oil suspension is monitored by UV fa HPLC. The content of the effective ingredient of the oil suspension is stability after one month. This oil suspension containing natural astaxanthin can be administered in the form of soft capsules.

(2) 200 g of the carotenoid compound crystal containing natural astaxanthin is mixed with modified starch and sucrose to prepare water-soluble microcapsule particles containing astaxanthin according to the method of CN101177540B. It may be found that the microcapsule particles have good stability, and the retention rate is higher than 95% in case of airtight package and storied at 40° C. for two years. It is shown from assays in vitro that the bioavailability of the microcapsule particles is increased nearly tenfold in comparison with the astaxanthin crystal. This microcapsule particles containing natural astaxanthin can be administered in the form of tablets or capsules.

It can be seen from the above Examples that the high content carotenoid crystal from *Adonis amurensis* are firstly illustrated in the present invention, wherein the high content carotenoid crystal contains a large amount of all trans (3 S, 3 S)-astaxanthin and a small amount of semi-astacene, astancene, adonirubin and trace amounts of other carotenoids, The carotenoid may be exist in dietary ingredients, and can be detected in human blood. This kind of carotenoid crystal has high purity, and can be used in multiple forms in the fields of dietary supplements of human being, food additives, feed additives and cosmetic products. The present invention also provides a method of preparing the high-content carptenoid compound from *Adonis amurensis* with simple and reliable, suitable for industrial production.

The present invention illustrates by the above examples, however, it is understood that, the present invention is not limited to special instance and implementation scheme described herein. Here the purpose including these special instances and implementation schemes is aimed at helping the persons skilled in the art to achieve this invention. It is easy for any persons skilled in the art to carry out further improvement and perfection not from the spirit and scope of the invention, so the present invention is just limited by the content and scope of claims of the present invention, its intention to cover all included all alternative solutions and equivalent solutions within the spirit and scope of the present invention limited by the appendix claims.

We claim:

1. A method of preparing a high-content carotenoid mixture by using *adonis amurensis* extract as raw material, characterized in that, comprising the following steps:

(a) mixing *Adonis amurensis* extract with alcohols solvent and fully dissolving, to obtain a mixed solution;

(b) heating the mixed solution of the step (a) to 25-75° C., and dropwise adding an alkali solution to the reaction, and the reaction time is 0.5~ 6.0 hr, wherein a concentration of the alkali solution of the reaction is 0.01-2.50 mol/L after adding dropwise the alkali solution;

(c) adding a mixture of alcohols solvent and water to obtain a reaction solution, after completion of the step (b), wherein a volume ratio of the alcohols solvent to water in the step (c) is 1:5-10;

(d) filtering the reaction solution of the step (c) to obtain a filter cake, and then washing the filter cake with a mixture of alcohols solvent and water, wherein a volume ratio of the alcohols solvent to water in the step (d) is 2-3:1; and (e) drying the filter cake of the step (d) in vacuum to obtain a carotenoid mixture;

wherein, in the high-content carotenoid mixture, the content of the total carotenoid is higher than 95 wt %, the proportion of the all-trans (3S, 3'S) astaxanthin in the carotenoid is higher than 80 wt %, the all-trans (3S, 3'S)-astaxanthin has the molecular structure as shown in formula (I):

(I)

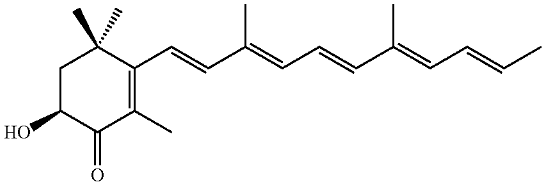

-continued

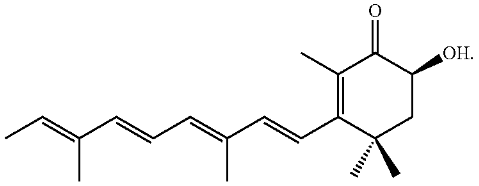

2. The method according to claim 1, characterized in that, in the step (a), the ratio of the volume of the alcohols solvent to the weight of *Adonis amurensis* extract is 25~40 times.

3. The method according to claim 1, characterized in that, in the step (b), the concentration of the alkali solution of the reaction is 1.00-2.00 mol/L after adding dropwise the alkali solution.

4. The method according to claim 2, characterized in that, wherein the alcohols solvent in the step (a) is ethanol, propylene glycol or glycerol; and the alkali solution in step (b) is sodium hydroxide solution, potassium hydroxide solution or sodium methoxide solution.

* * * * *